United States Patent [19]

Photis et al.

[11] 4,080,275

[45] Mar. 21, 1978

[54] PHOTOPOLYMERIZABLE BENZOYL BENZOATE COMPOSITIONS

[75] Inventors: James A. Photis, Ridgefield, Conn.; Francis A. Via, Yorktown Heights, N.Y.

[73] Assignee: Stauffer Chemical Company, Westport, Conn.

[21] Appl. No.: 817,089

[22] Filed: Jul. 18, 1977

[51] Int. Cl.$^2$ .............................. C08F 2/46; C08F 4/00
[52] U.S. Cl. .............................. 204/159.23; 96/115 P; 204/159.1 B; 260/22 CB; 260/837 R
[58] Field of Search .................... 204/159.18, 159.23; 96/115 P

[56] References Cited

U.S. PATENT DOCUMENTS

| 3,926,638 | 12/1975 | Rosen et al. | 96/115 R |
| 4,017,652 | 4/1977 | Gruber | 427/54 |
| 4,024,296 | 5/1977 | Gruber | 427/53 |

FOREIGN PATENT DOCUMENTS 1,223,463  2/1971  United Kingdom.

OTHER PUBLICATIONS

Chemical Abstracts, vol. 82, 1975, No. 113, 348f.

*Primary Examiner*—Richard B. Turer
*Attorney, Agent, or Firm*—E. P. Trevors; D. S. Ortiz

[57] ABSTRACT

A photopolymerizable composition comprising photopolymerizable ethylenically unsaturated compounds and, as the photoinitiator, a benzoyl benzoate having the formula:

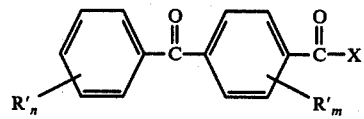

wherein X is OR, NHR or NRR; R is an independently selected hydrocarbon of 1 to 30 carbon atoms, alkoxysubstituted alkyl of 2 to 12 carbon atoms or aminosubstituted alkyl of 2 to 12 carbon atoms; R' is an independently selected halogen or X; and $n$ and $m$ are independently selected integers from 0 to 3.

28 Claims, No Drawings

PHOTOPOLYMERIZABLE BENZOYL BENZOATE COMPOSITIONS

BACKGROUND OF THE INVENTION

This invention relates to photopolymerizable compositions and to a method employing same. More particularly, this invention relates to the use of certain benzoyl benzoates as photoinitiators for ethylenically unsaturated compounds.

Photopolymerization of unsaturated compositions wherein a photoinitiating compound is included in the polymerizable mass is well known in the art. The process has many advantages over thermal polymerization and is particularly useful where long holding life combined with rapid hardening at low temperature is desirable. Photoinitiating compounds must absorb light and utilize the energy so acquired to initiate polymerization.

A large number of compounds have been found useful as photoinitiators for the polymerization of unsaturated compounds. Among those heretofore in most common usage in industry are the benzoin ethers of primary and secondary alcohols such as methyl alcohol, ethyl alcohol, isopropyl alcohol and isobutyl alcohol.

While particular industrial applications often dictate certain requisite characteristics, the primary determinants of universal application in the selection of a suitable photoinitiating compound are its level of reactivity and its effect upon storage stability when combined with the photopolymerizable medium wherein it is to function. This latter characteristic is significant in view of the desirability of one-component systems which will not gel prior to use.

While compounds in common use as photoinitiators do effect rates of polymerization which are industrially acceptable and render photopolymerization superior to thermal polymerization in various applications, methods of achieving increased polymerization rates with increased stability are constantly being sought. Improved photoinitiators are particularly desirable since photopolymerization techniques are gaining increasingly widespread acceptance due to the inherently lower equipment costs, reduction of volatile emissions and reduced energy consumption which attend their use.

Thus, the ethers of benzoin, which are widely used as photoinitiating compounds, are not wholly satisfactory with regard to the one-component system storage stability factor. Any unsaturated system to which a benzoin ether is added has considerably diminished dark storage stability and will gel prematurely. Various attempts have been made to remedy this deficiency of the benzoin compounds by including stabilizing additives in the polymerization system. Thus, U.S. Pat. No. 3,819,495 discloses the addition of organic chlorine containing compounds and copper compounds as a stabilization system while U.S. Pat. No. 3,819,496 teaches the use of organic chlorine compounds with iron and/or manganese compounds for that purpose, Many other stabilizers have been suggested and, while some improvements have been achieved in the stability of unsaturated systems containing benzoin-type photoinitiators, the necessity of incorporating stabilizing additives raises the cost of such systems appreciably while the results are still not wholly satisfactory.

Thus, various aromatic compounds have been proposed as photoinitiators for unsaturated compounds. For example, U.S. Pat. No. 3,715,293 teaches the use of acetophenone compounds such as 2,2-diethoxyacetophenone, while a series of patents including U.S. Pat. Nos. 3,926,638; 3,926,639; 3,926,640; 3,926,641; 4,022,674; 4,004,998; 4,008,138 and 4,028,204 describe complex compounds derived from benzophenone. As an example of the benzophenone-derived materials, U.S. Pat. No. 3,404,998 describes photoinitiators made by reacting carboxy-substituted benzophenones with hydroxyl-containing polyethylenically unsaturated esters, while U.S. Pat. Nos. 3,926,639 and 4,028,204 describe a benzophenone substituted with a carboxy group and an ester group which is reacted with certain resins, such as alkyds, polyesters, polyethers, polyamides and epoxies, to provide the photoinitiator.

Another approach is disclosed in U.S. Pat. No. 3,759,807 where certain benzophenones which must be used with activators are disclosed. Also representative of benzophenone systems is Brit. Pat. No. 1,223,463 which teaches the addition of diketones such as m-benzoylbenzophenone, ethylene glycol bis (p-benzoylbenzoate) or diethylene glycol bis (p-benzoylbenzoate) to nylon to give photosensitive materials suitable for the preparation of printing plates.

In U.S. Pat. No. 4,017,652, ethyl benzoylbenzoate is disclosed as a photosensitizer which must be used in connection with a photoinitiator such as a benzoin ether.

With regard to rate of polymerization and the dark storage stability of the uncured system, none of the most widely used photoinitiating compounds is wholly acceptable in unsaturated systems.

Now it has been found in accordance with this invention that certain benzoyl benzoates and benzamides are excellent photoinitiators for ethylenically unsaturated compounds. These photoinitiators provide polymerizable systems not subject to premature gelation. Furthermore, these photoinitiators are reactive in many different systems based on ethylenically unsaturated compounds.

SUMMARY OF THE INVENTION

The photopolymerizable composition of this invention comprises an ethylenically unsaturated compound and a p-benzoyl benzoate or a p-benzoyl benzamide. After applying the compositions to the desired substrate, curing is effected by exposure to actinic radiation.

DETAILED DESCRIPTION OF THE INVENTION

More in detail, the photopolymerizable composition of this invention comprises an ethylenically unsaturated monomer and, as the photoinitiator, a p-benzoyl benzoate or benzamide having the formula:

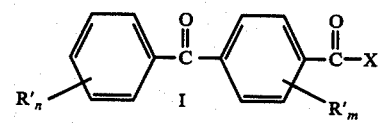

wherein X is OR, NHR or NRR; R is an independently selected hydrocarbon of 1 to 30 carbon atoms, alkoxysubstituted alkyl of 2 to 12 carbon atoms; R' is an independently selected halogen or X; and $n$ and $m$ are independently selected integers from 0 to 3.

In the foregoing definition, the term "hydrocarbon of from 1 to 30 carbon atoms" refers to straight and branched chain acyclic hydrocarbon groups which may contain unsaturated carbon-to-carbon bonds.

Illustrative compounds I include, but are not limited to, methyl-p-benzoylbenzoate; tridecyl-p-benzoylbenzoate; (2-propenyl)-p-benzoylbenzoate; (3-pentenyl)-p-benzoylbenzoate; methoxymethyl-p-benzoylbenzoate; (2-ethoxyethyl)-p-benzoylbenzoate; aminoethyl-p-benzoylbenzoate; (2-aminopropyl)-p-benzoylbenzoate; (dimethylaminopropyl)-p-benzoylbenzoate;N-methyl-p-benzoylbenzamide; N-tridecyl-p-benzoylbenzamide; N-(2-propenyl)-p-benzoylbenzamide; N-(3-pentenyl)-p-benzoylbenzamide; N-methoxymethyl-p-benzoylbenzamide; N-(2-ethoxyethyl)-p-benzoylbenzamide; N-aminoethyl-p-benzoylbenzamide; N-(2-aminopropyl)-p-benzoylbenzamide; N-(dimethylaminopropyl)-p-benzoylbenzamide; 4-carbobutoxy-4'-fluorobenzophenone; 4-carbobutoxy-3-bromobenzophenone, 4-carboethoxy-3,4,4'-trichlorobenzophenone; 4-carbobutoxy-4'-carboethoxybenzophenone; etc.

The benzoyl benzoates and benzamides I are known compounds, some of which are commercially available. Alternately, they are readily prepared by methods described in the literature. Thus, for example, they can be prepared by the techniques described in Advanced Organic Chemistry: Reactions, Mechanisms and Structure, J. March ed., McGraw Hill, New York (1968). The esters can also be prepared by the procedure of D. Bichan and M. Winnik, Tetrahedron Letters, 3857 (1974).

The compositions curable by actinic radiation according to the invention can contain a photopolymerizable polymer in a reactive ethylenically unsaturated monomeric medium, a reactive polymer alone, a reactive monomer alone, or any of these combined with an inert solvent. Additionally, the polymerizable composition can contain any of the pigments commonly used in photopolymerization techniques.

Polymerizable ethylenically unsaturated compounds which are useful in practicing the invention are acrylic, α-alkacrylic and α-chloroacrylic acid compounds such esters, amides and nitriles. Examples of such compounds are acrylonitrile, methacrylonitrile, methyl acrylate, ethyl acrylate, methyl methacrylate, isobutyl methacrylate, 2-ethylhexyl acrylate, methacrylamide and methyl α-chloroacrylate. Also useful, although not preferred due to their slower rates or reactivity, are vinyl and vinylidene esters, ethers and ketones. Additionally, compounds having more than one terminal unsaturation can be used. Examples of these include diallyl phthalate, diallyl maleate, diallyl fumarate, triallyl cyanurate, triallyl phosphate, ethylene glycol dimethacrylate, glycerol trimethacrylate, pentaerythritol triacrylate, pentaerythritol tetraacrylate, trimethylolpropane triacrylate, metacrylic anhydride and allyl ethers of monohydroxy or polyhydroxy compounds such as ethylene glycol diallyl ether, pentaerythritol tetraallyl ether, and the like. Nonterminally unsaturated compounds such as diethyl fumarate can similarly be used.

The acrylic acid derivatives are particularly well suited to the practice of the invention and are consequently preferred components as monomers in monomer-containing polymerizable systems and as reactive centers in polymerizable polymers. While monomeric styrene can be used in the practice of the invention, it is not a preferred constituent of systems polymerizable thereby due to its slow rate of reaction.

Additionally, the photopolymerizable composition can contain a sensitizer capable of enhancing the photoinitiating reactivity of the photoinitiating compound of the invention by triplet sensitization. Examples of sensitizers useful in the practice of the invention are such compounds are biphenyl, xanthone, thioxanthone, acetophenone and the like. These are typically added in amounts ranging from about 0.1 to about 6 weight percent. The techniques whereby such sensitizers are selected for use in conjunction with particular photoinitiators are well known in the art. See, for example, MUROV, Handbook of Photochemistry, Marcel Dekker, Inc., N.Y. (1973).

Additionally polymerization promoters such as organic amines can be used to accelerate cure rates, either alone or in combination with a sensitizer. Such amines can be primary, secondary, or preferably, tertiary, and can be represented by the general formula:

$$R^1R^2R^3N$$

wherein $R^1$ and $R^2$ are independently selected hydrogen, straight chain or branched alkyl having from 1 to about 12 carbon atoms, straight chain or branched alkenyl having from 2 to about 12 carbon atoms, cycloalkyl having from 3 to about 10 ring carbon atoms, cycloalkenyl having from 3 to about 10 ring atoms, aryl having from 6 to about 12 ring carbon atoms, alkaryl having 6 to about 12 ring carbon atoms; $R^3$ has the same meaning as $R^1$ and $R^2$ with the exception that it cannot be hydrogen and that it cannot be aryl when both $R^1$ and $R^2$ are aryl. Also, when taken together $R^2$ and $R^3$ can be divalent alkylene group having from 2 to about 12 carbon atoms, a divalent alkenylene group having from 3 to about 10 carbon atoms, a divalent alkadienylene group having from 5 to about 10 carbon atoms, a divalent alkatrienylene group having from 5 to about 10 carbon atoms, a divalent alkyleneoxyalkylene group having a total of from 4 to about 12 carbon atoms, or a divalent alkyleneaminoalkylene group having a total of from 4 to about 12 carbon atoms. As previously indicated, the amines can be substituted with other groups; thus, the $R^1$, $R^2$ and $R^3$ variables, whether taken singly or together, can contain one or more substituents thereon. The nature of such substituents is generally not of significant importance and any substituent group can be present that does not exert a pronounced deterrent effect on the ultraviolet crosslinking reaction.

Exemplary suitable organic amines are methylamine, dimethylamine, triethylamine, isopropylamine, triisopropylamine, tributylamine, t-butylamine, 2-methylbutylamine, N-methyl-N-butylamine, di-2-methylbutylamine, tri-2-ethylhexylamine, dodecylamine, tri-2-chloroethylamine, di-2-bromoethylamine, methanolamine, triethanolamine, methyldiethanolamine, propanolamine, triisopropanolamine, butylethanolamine, dihexanolamine, 2-methoxyethylamine, 2-hydroxyethyldiisopropylamine, allylamine, cyclohexylamine, trimethylcyclohexylamine, bis-methylcyclopentylamine, tricyclohexadienylamine, N-methyl-N-cyclohexylamine, N-2-ethylhexyl-N-cyclohexylamine, diphenylamine, methylphenylamine, trixylyl-amine, tribenzylamine, triphenethylamine, benzyldimethyl, N-methylethylenimine, N-cylohexylethyl-enimine, piperidine, N-ethylpiperidine, 1,2,3,4-tetrahydropyridine, 2-, 3- and 4-picoline, morpholine, N-methyl morpholine, N-2-hydroxyethylmorpholine, piperazine, N,N''-dimethylpiperazine, 2,2-dimethyl-1,3-bis [3 (N-morpholinyl-propionyloxy]-propane, and the like. The preferred organic amines are the tertiary amines, with the alkanol amines being most preferred.

Thus it is seen that the constitution of photopolymerizable compositions which can be used in the practice of the invention is widely variable. However, the compounds enumerated above are purely illustrative. Materials subject to polymerization by actinic radiation as well as permissable variations and substitutions of equivalent components within particular types of compositions are well known to those skilled in the art.

The photoinitiators of the invention can be utilized in amounts ranging from 0.01 to about 30 percent by weight based on the photopolymerizable composition. However, preferably amounts of the compounds are between 1.0 and 10.0 weight percent.

The process can be carried out by mixing a quantity of a photoinitiating compound of the invention with a photopolymerizable composition and exposing the resultant mixture to actinic radiation. Alternatively, a one-component system comprising the photopolymerizable composition, the photoinitiator of the invention and, if desired, pigmentation, can be stored in the dark for a prolonged period of time prior to use without fear of gelation.

A preferred manner of practicing the invention is by the use of photopolymerizable molding and coating compositions which consist of mixtures of unsaturated polymeric compounds and monomeric compounds copolymerizable therewith. The polymeric compounds can be conventional polyesters prepared from unsaturated polycarboxylic acids such as maleic acid, fumaric acid, glutaconic acid, itaconic acid, citraconic acid, mesaconic acid and the like, and polyhydric alcohols such as ethylene glycol, diethylene glycol, glycerol, propylene glycol, 1,2-butanediol, 1,4-butanediol, pentaerythritol, trimethylolpropane and the like. The carboxylic acid content can also contain saturated components. The inclusion of a monobasic fatty acid content, either as such or in the form of a triglyceride or oil, in the photopolymerizable polyester composition to comprise an alkyd resin is also acceptable. These resins can, in turn, be modified by silicones, epoxides, isocyanates, etc., by known techniques.

The compositions of the instant invention after being prepared in the ratios as set out above can be applied to the material to be coated by conventional means, including brushing, spraying, dipping and roll coating techniques, and may, if desired, be dried under ambient or elevated conditions to provide coatings on the substrate. The substrate can be of any composition, including but not limited to plastic, fiber, ceramic, glass, etc.

After the composition is applied to the desired substrate, it is exposed to light radiation having wave lengths of above about 2000 Angstrom units, preferably from about 2000 up to about 8000 Angstroms, and most preferably between about 2400 Angstroms and 5400 Angstroms. Exposure should be from a source located about 1 to 5 inches from the coating for a time sufficient to cause crosslinking of the composition.

The light radiation can be ultraviolet light generated from low, medium, and high pressure mercury lamps. This equipment is readily available and its use is well known to those skilled in the art. Other sources could include electron beam radiation, plasma arc, laser beams, etc.

While any of the compounds having the formula I can be used in the practice of this invention, preferred are those compounds where $m$ and $n$ are 0; R is alkyl of 1 to 12 carbon atoms, alkenyl of 3 to 5 carbon atoms, alkoxysubstituted alkyl of 2 to 4 carbon atoms or aminosubstituted alkyl of 2 to 5 carbon atoms. Particularly preferred are the p-benzoylbenzoates, i.e., compounds I where X is 0.

In the following examples, which will serve to illustrate the practice of this invention, all parts and percentages are by weight unless otherwise specified.

EXAMPLE 1

To a magnetically stirred solution of 5.0 grams (0.022 mole) of p-benzoylbenzoic acid in benzene was added 5.0 grams (0.024 mole) of phosphorous pentachloride. After heating under reflux all volatile components were removed on a rotary evaporator. To the residual solid p-benzoyl benzoic acid chloride was added methanol and the mixture was warmed briefly to cause dissolution. All volatiles were once again removed on a rotary evaporator to provide 5.2 grams of a white solid, representing a 98% yield of methyl-p-benzoylbenzoate. The infrared spectrum showed carbonyl bands at 1650 and 1715 cm$^{-1}$ and the absence of a carboxylic acid band at 3300 – 2000 cm$^{-1}$, confirming the formation of methyl-p-benzoylbenzoate.

To a standard test solution consisting of 42% by weight of trimethylolpropane triacrylate, 17% by weight of ethylhexyl acrylate and 41% by weight of ACTOMER X.80 ® Resin, an unsaturated long chain linseed oil alkyd resin, available from Union Carbide Corporation, was added 4.0% by weight of methyl p-benzoylbenzoate.

Cure rates were determined in air using as a source of actinic light a PPG Model QC 1202 AN UV Processor manufactured by PPG Industries, Inc. The radiation source for this apparatus consists of two high intensity medium pressure quartz mercury lamps 12 inches in length and each operating at a linear power density of about 200 watts per inch or 2400 watts per lamp. The lamps are housed in an elliptical reflector above a variable speed conveyor belt and each lamp provides a 2-inch band of high flux actinic radiation on the conveyor. This 2-inch exposure area is bordered on both sides by an additional 2-inch area of medium flux energy for a total radiation area of 6 inches for each lamp. In the curing data presented below, cure rate of the polymerizable composition is presented in feet-per-minute-per-lamp (ft./min./lamp). Thus, a conveyor belt speed of one foot/min. will, with a 12-inch exposure area for the two lamps, provide 60 seconds of exposure or a cure rate of 0.5 ft./min./lamp. Similarly, a belt speed of 10 ft./min. will provide 6 seconds of exposure or a rate of 5.0 ft./min./lamp while a speed of 20.0 ft./min. will give 3 seconds exposure or a rate of 10 ft./min./lamp etc.

The composition had a cure rate of 20 ft./min./lamp.

EXAMPLE 2

To a mechanically stirred solution of 1000 grams (7.12 moles) of benzoyl chloride in 6000 grams of toluene was added 1000 grams (7.50 moles) of anhydrous aluminum chloride over a 20–30 minute period. The temperature of the reaction mixture rose to near the boiling point during the addition, and heating at reflux was maintained for three additional hours. After cooling, 1200 milliliters of water were added, slowly at first, followed by 1000 milliliters of concentrated hydrochloric acid. The organic layer was separated, washed twice with hot water and concentrated on a rotary evaporator. Vacuum distillation of the residual oil provided 1300 grams (93% yield) of white, semi-solid methyl benzophenone; (b.p. 180°-200° C., 10-15 mm Hg; m.p. 50° C.) The infrared spectrum revealed a carbonyl band at 1665 cm$^{-1}$.

The amount of 1300 grams (6.65 moles) of methyl benzophenone was then melted and heated to 170°-180° C. in the 2 liter two necked round bottom flask with magnetic stirring. Chlorine gas was introduced through a gas dispersion tube immersed below the liquid at a rate such that the characteristic greenish color in chlorine was not detectable in the exiting stream of hydrogen chloride. After 12 hours, the hot melt was poured into 8 liters of isopropyl alcohol. This mixture was chilled to −5° to 0° C. and the precipitated solid removed by suction filtration to provide 1600 grams (81% yield) of 4-(trichloromethyl)benzophenone, mp 190°-111° C. A carbonyl band at 1670 cm$^{-1}$ was noted in the infrared spectrum.

A mixture of 1600 grams (5.35 moles) of the 4-(trichloromethyl)benzophenone, 4000 milliliters of n-butanol and 2400 milliliters of 19% by weight aqueous hydrochloric acid was mechanically stirred at the reflux temperature for three hours. Then three liters of water was added. The upper organic layer was separated and stirred with 4000 milliliters of 10% aqueous sodium carbonate solution. The organic layer was again separated and washed twice with hot water. Removal of volatile components under reduced pressure produced 1400 grams (93% yield) of semi-solid, off-white n-butyl-p-benzoylbenzoate, m.p. 50°-60° C. Carbonyl bands in the infrared spectrum at 1670 and 1730 cm$^{-1}$ confirmed the structure of the product.

Varying concentrations of the n-butyl-p-benzoylbenzoate were added to samples of the standard test solution described in Example 1; the cure data is presented below. Where ranges for cure rates are indicated, several samples were tested, with purer esters giving the faster rates.

| SAMPLE | CONCENTRATION (% Wt.) OF n-BUTYL-p-BENZOYLBENZOATE | CURE RATE (Ft./Min./Lamp) |
|---|---|---|
| 1 | 2 | 7.5 – 10 |
| 2 | 4 | 15 – 20 |
| 3 | 6 | 20 |
| 4 | 8 | 30 – 35 |
| 5 | 10 | 30 |

EXAMPLE 3

The amount of 4% by weight of the n-butyl-p-benzoylbenzoate prepared in Example 2 was added to resin samples comprising 50% by weight of EPOCRYL ® Resin DRH-303, a diacrylate ester of Bisphenol A epoxy resin available from Shell Chemical Company, and 50% by weight of 1,6-hexanediol diacrylate available from Celenese Corporation. A cure rate ranging from 30 to 40 ft./min./lamp was obtained for several samples.

COMPARATIVE EXAMPLES

In order to demonstrate the efficacy of the para esters of this invention, the ortho and meta isomers of the ester of Example 2 were prepared and tested. The n-butyl-o-benzoylbenzoate was prepared by the acid-catalyzed esterification of o-benzoyl benzoic acid. The n-butyl-m-benzoylbenzoate was prepared following the procedure and employing the ingredients described in Example 2 but substituting m-toluyl chloride for benzoyl chloride and benzene for toluene. The cure data for 4% by weight loading is presented below.

| ESTER | CURE RATE TMPTA/EHA ACTOMER X-80 ®[1] | (Ft./Min./Lamp) EPOCRYL RESIN DRH-303/HDDA[2] |
|---|---|---|
| n-butyl-o-benzoylbenzoate | 5 – 7.5 | 0 |
| n-butyl-m-benzoylbenzoate | 5 | 10 |

[1]42% by weight of trimethylolpropane triacrylate, 17% by weight of ethylhexyl acrylate and 41% by weight of ACTOMER X- ® Resin, an unsaturated long chain linseed oil alkyd resin, available from Union Carbide Corporation.
[2]50% by weight of EPOCRYL ® Resin DRH-303, a diacrylate ester of Bisphenol A epoxy resin available from Shell Chemical Company, 50% by weight 1,6-hexanediol diacrylate available from Celenese Corporation.

EXAMPLE 4

Following the procedure of Example 1, but employing 4-methylpentanol instead of methanol, the ester (4-methylpentyl)-p-benzoylbenzoate was prepared. The structure was confirmed by the presence of carbonyl bands at 1670 and 1730 cm$^{-1}$ in the infrared spectrum. When this ester was added at a level of 4% by weight to the test solution of Example 1, a cure rate of 15 ft./min./lamp was obtained.

EXAMPLE 5

A solution of 5.0g (0.020 mole) of p-benzoylbenzoic acid chloride made as described in Example 1, in 75 ml of pyridine was magnetically stirred at ambient temperature and treated at once with excess n-pentanol (5–10 milliliters). After 30 minutes, cold dilute hydrochloric acid and ether was added. The organic layer was separated, washed with dilute hydrochloric acid until the washing was acidic to litmus paper and dried over anhydrous magnesium sulfate. Gravity filtration and concentration on a rotary evaporator produced a greenish-yellow colored oil. The excess alcohol was removed under vacuum with warming to afford an essentially quantitative yield of n-pentyl-p-benzoyl benzoate showing carbonyl absorbtion bands in the infrared spectrum at 1725 and 1670 cm.$^{-1}$ A cure rate of 20 ft./min./lamp was obtained at a 4% weight loading in the test solution of Example 1.

In order to demonstrate the dark-storage stability of this compound, 4% by weight was added to another sample of the test solution. A glass jar was filled to greater than 90% by volume with the composition, with was then stored in the dark at 65° C. The composition had not gelled when inspected after 3 months storage.

EXAMPLE 6 n-Octyl-p-benzoylbenzoate was prepared by reacting p-benzoylbenzoic acid chloride with n-octanol. The presence of carbonyl bands at 1725 and 1670 cm$^{-1}$ in the infrared spectrum confirmed that the product had been obtained. The test solution of Example 1 was employed and the ester was added at a level of 4% by weight; a cure rate of 17.5 ft./min./lamp was obtained.

EXAMPLE 7

Tridecyl-p-benzoylbenzoate was prepared from para-benzoyl-benzoic acid chloride and tridecanol. The infrared spectrum revealed carbonyl bands at 1725 and 1670 cm$^{-1}$. A cure rate of 15 ft./min./lamp was obtained at a 4% by weight loading in the test solution of Example 1.

EXAMPLE 8

(2-Ethoxyethyl)-p-benzoylbenzoate was prepared from para-benzoyl benzoic acid chloride and 2-ethoxyethanol. The structure of the product was confirmed by the presence of carbonyl bands in the infrared spectrum at 1670 and 1730 cm$^{-1}$. When added at 4% by weight loading to the solution described in Example 1, a cure rate of 15 ft./min./lamp was obtained. A sample in the same test solution was stable after three months storage following the procedure described in Example 5.

EXAMPLE 9

(2-Dimethylaminoethyl)-p-benzoylbenzoate was prepared from para-benzoylbenzoic acid chloride and 2-dimethylaminoethanol. The structure of the product was confirmed by the presence of carbonyl absorption bands in the infrared spectrum at 1670 and 1725 cm$^{-1}$. When added at 4% by weight loading to the test solution described in Example 3, a cure rate of 40 ft./min./lamp was observed.

EXAMPLE 10

3-(Dimethylaminopropyl)-p-benzoylbenzoate was prepared from para-benzoylbenzoic acid chloride and 3-dimethylaminopropanol. The structure of the product was confirmed by the presence of carbonyl bands in the infrared spectrum at 1670 and 1730 cm$^{-1}$. At a 4% by weight loading, this ester resulted in a cure rate of 15 ft./min./lamp in the test solution of Example 1 and a cure rate of 50 ft./min./lamp in the test solution of Example 3.

EXAMPLE 11

A mixture of 10.0 grams (0.044 mole) of p-benzoylbenzoic acid, 100 milliliters of n-propanol and 0.25 milliliters of concentrated sulfuric acid was stirred under reflux for 5 hours. Aqueous sodium bicarbonate solution was then added. The organic layer was separated, dried over anhydrous magnesium sulfate and filtered. Volatiles were removed under vacuum with warming to provide 9.0 grams (76.3% yield) of n-propyl-p-benzoylbenzoate. The infrared spectrum revealed carbonyl absorption bands at 1670 and 1730 cm$^{-1}$.

At a loading of 4% by weight in the test solution of Example 3, this ester exhibited a cure rate of 25 ft./min./lamp.

EXAMPLE 12

Following the procedure of Example 2, iso-butyl-p-benzoylbenzoate was prepared from 20 grams of p-benzoyl benzotrichloride, 50 milliliters of iso-butanol and 30 milliliters of 19 percent by weight aqueous hydrochloric acid. When added at a loading of 4% by weight to the test solution described in Example 3, a cure rate of 30–35 ft./min./lamp was observed for several samples.

EXAMPLE 13

Following the procedure of Example 6, (4-pentenyl)-p-benzoylbenzoate was prepared from p-benzoylbenzoic acid chloride and 4-pentenol. The structure of the product was confirmed by the presence of carbonyl bands in the infrared spectrum at 1670 and 1730 cm$^{-1}$. At a loading of 4% by weight, a cure rate of 15 ft./min./lamp was obtained in the test solution described in Example 1.

EXAMPLE 14

N,N-diethyl-p-benzoyl benzamide was prepared by reacting p-benzoylbenzoic acid chloride with diethylamine. At a 4% by weight loading in the test solution described in Example 1 a cure rate of 7.5 – 10 ft./min./lamp was observed for several samples.

EXAMPLE 15

N-iso-butylamine was reacted with p-benzoylbenzoic acid chloride to provide N-iso-butyl-p-benzoyl benzamide. At a 4% by weight loading in the test solution described in Example 1, a cure rate of 7.5 – 10 ft./min./lamp was observed for several samples.

EXAMPLE 16

N,N-di-n-butyl-p-benzoyl benzamide was prepared from p-benzoylbenzoic acid chloride and di-n-butylamine. A cure rate of 10 ft./min/lamp was observed at a 4% by weight loading in the test solution described in Example 1. A rate of 5 ft./min./lamp was observed at the same loading in the test solution described in Example 3.

What is claimed is:

1. A photopolymerizable composition comprising an ethylenically unsaturated compound and a photoinitiating amount of a p-benzoyl benzoate or benzamide of the formula:

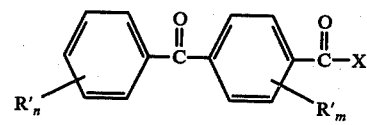

wherein X is OR, NHR or NRR; R is an independently selected hydrocarbon of 1 to 30 carbon atoms, alkoxysubstituted alkyl of 2 to 12 carbon atoms or aminosubstituted alkyl of 2 to 12 carbon atoms; R' is an independently selected halogen or X; and $n$ and $m$ are independently selected integers from 0 to 3.

2. The composition of claim 1 wherein said benzoyl benzoate comprises between about 0.01 to about 30 percent by weight of said compositions.

3. The composition of claim 2 wherein X is oxygen and $m$ and $n$ are 0.

4. The composition of claim 3 wherein R is alkyl.

5. The composition of claim 4 wherein said benzoyl benzoate is methyl-p-benzoyl benzoate.

6. The composition of claim 4 wherein said benzoyl benzoate is n-propyl-p-benzoyl benzoate.

7. The composition of claim 4 wherein said benzoyl benzoate is iso-propyl-p-benzoyl benzoate.

8. The composition of claim 4 wherein said benzoyl benzoate is n-butyl-p-benzoyl benzoate.

9. The composition of claim 4 wherein said benzoyl benzoate is iso-butyl-p-benzoyl benzoate.

10. The composition of claim 4 wherein said benzoyl benzoate is (4-methylpentyl)-p-benzoyl benzoate.

11. The composition of claim 4 wherein said benzoyl benzoate is n-octyl-p-benzoyl benzoate.

12. The composition of claim 4 wherein said benzoyl benzoate is tridecyl-p-benzoyl benzoate.

13. The composition of claim 3 wherein R is alkenyl of 3 to 5 carbon atoms.

14. The composition of claim 13 wherein said benzoyl benzoate is (4-pentenyl)-p-benzoyl benzoate.

15. The composition of claim 3 wherein R is alkoxysubstituted alkyl of 2 to 4 carbon atoms.

16. The composition of claim 15 wherein said benzoyl benzoate is (2-ethoxyethyl)-p-benzoylbenzoate.

17. The composition of claim 3 wherein R is aminosubstituted alkyl of 2 to 5 carbon atoms.

18. The composition of claim 17 wherein said benzoyl benzoate is (2-dimethylaminoethyl)p-benzoyl benzoate.

19. The composition of claim 17 wherein said benzoyl benzoate is (2-dimethylaminopropyl)-p-benzoyl benzoate.

20. The composition of claim 2 wherein X is nitrogen and $m$ and $n$ are 0.

21. The composition of claim 20 wherein R is alkyl.

22. The composition of claim 21 wherein said benzoylbenzamide is iso-butyl-p-benzoylbenzamide.

23. The composition of claim 21 wherein said benzoylbenzamide is diethyl-p-benzoylbenzamide.

24. The composition of claim 23 wherein said benzoylbenzamide is di-n-butyl-p-benzoylbenzamide.

25. In the method of photopolymerizing an ethylenically unsaturated compound in the presence of a photoinitiator by exposure to actinic radiation, the improvement which comprises employing as said photoinitiator a p-substituted benzoyl benzoate or benzamide of the formula:

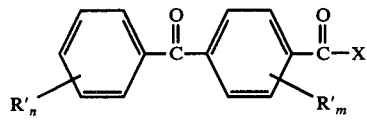

wherein X is OR, NHR or NRR; R is an independently selected hydrocarbon of 1 to 30 carbon atoms, alkoxysubstituted alkyl of 2 to 12 carbon atoms or aminosubstituted alkyl of 2 to 12 carbon atoms; R' is an independently selected halogen or X; and $n$ and $m$ are independently selected integers from 0 to 3.

26. The method of claim 23 wherein said benzoyl benzoate or benzamide comprises between about 0.01 to about 30 percent by weight of said composition.

27. The method of claim 26 further including a promoter.

28. The method of claim 27 wherein said promoter is an organic amine.

* * * * *

UNITED STATES PATENT AND TRADEMARK OFFICE
CERTIFICATE OF CORRECTION

PATENT NO. : 4,080,275
DATED : 3/21/78
INVENTOR(S) : J. M. Photis, F. A. Via

It is certified that error appears in the above-identified patent and that said Letters Patent are hereby corrected as shown below:

In the inventor's name - James A Photis should read ---James "M" Photis---.

To the end of the title ADD "AND PROCESS".

Col. 1, line 59 should have a period, not a comma after purpose.

Col. 2, Line 44, Underline is missing under "$\underline{p}$"-benzoyl and "$\underline{p}$"benzamide.

Col. 2, Line 53, Underline is missing under "$\underline{p}$"benzoyl benzoate

Col. 3, Line 4 Underline is missing under methyl-"$\underline{p}$"-benzoylbenzoate; and tridecyl-$\underline{p}$-benzoylbenzoate Col. 3, Line 5, Underline is missing under (2-propenyl)-"$\underline{p}$"benzoylbenzoate;

Col. 3, Line 5, Underline is missing under (3-pententyl)-"$\underline{p}$"benzoyl-benzoate;

Col. 3, Line 6, Underline is missing under methoxymethyl-"$\underline{p}$"benzoylbenzoate;

Col. 3, Line 7, Underline is missing under (2-ethoxyethyl)-"$\underline{p}$"benzoylbenzoate;

UNITED STATES PATENT AND TRADEMARK OFFICE
CERTIFICATE OF CORRECTION

PATENT NO. : 4,080,275
DATED : 3/21/78
INVENTOR(S) : J. M. Photis, F. A. Via

It is certified that error appears in the above-identified patent and that said Letters Patent are hereby corrected as shown below:

Col. 3, Line 7, Underline is missing under aminoethyl-"p"benzoylbenzoate;

Col. 3, Line 8, Underline is missing under (2-amino-propyl)-"p"-benzoylbenzoate;

Col. 3, Line 9, Underline is missing under (dimethyl-aminopropyl)-"p"-benzoylbenzoate;

Col. 3, Line 10, Underline is missing under N-tridecyl-"p"-benzoylbenzamide;

Col. 3, Line 11, Underline is missing under N-(3-pentenyl)-"p"-benzoylbenzamide;

Col. 3, Line 12, Underline is missing under N-methoxy-methyl-"p"-benzoylbenzamide;

Col. 3, Line 13, Underline is missing under N-(2-ethoxy-ethyl)-"p"-benzoylbenzamide;

Col. 3, Line 14, Underline is missing under N-amino-ethyl-"p"benzoylbenzamide;

Col. 3, Line 15, Underline is missing under N-(dimethyl-aminopropyl)-"p"-benzoylbenzamide;

UNITED STATES PATENT AND TRADEMARK OFFICE
CERTIFICATE OF CORRECTION

PATENT NO. : 4,080,275
DATED : 3/21/78
INVENTOR(S) : J. M. Photis, F. A. Via

Page 3 of 7

It is certified that error appears in the above-identified patent and that said Letters Patent are hereby corrected as shown below:

Col. 3, Line 47, after "rate" should be "of" instead of "or".

Col. 6, Line 6, change "O" to "OR".

Col. 6, Line 5, Underline is missing under "p"-benzoylbenzoates.

Col. 6, Line 13, Underline is missing under "p"-benzoylbenzoin.

Col. 6, Line 17, Underline is missing under "p"-benzoyl.

Col. 6, Line 21, Underline is missing from methyl-"p" benzoylbenzoate.

Col. 6, Line 25, Underline is missing from methyl-"p"-benzoylbenzoate.

Col. 6, Line 32, Underline is missing from methyl-"p"-benzoylbenzoate.

Col. 7, Line 11, After color should be "of" instead of "in".

UNITED STATES PATENT AND TRADEMARK OFFICE
CERTIFICATE OF CORRECTION

PATENT NO. : 4,080,275

DATED : 3/21/78

INVENTOR(S) : J. M. Photis, F. A. Via

It is certified that error appears in the above-identified patent and that said Letters Patent are hereby corrected as shown below:

Col. 7, Line 17, "190" should be "109"

Col 7, Line 21, Underline is missing from n-butanol

Col 7, Line 31, Underline is missing from n-butyl-"p"-benzoylbenzoate

Col. 7, Line 34, Underline is missing from n-butyl-"p"-benzoylbenzoate

Col. 7, Table Heading: p should be underlined in n-Butyl-p-Benzoylbenzoate

Col. 7, Line 51, Underline is missing from n-butyl-"p"-benzoyl

Col 7, Line 61, para should be underlined "para"

Col 7, Line 62, ortho and meta should be underlined.

Col 7, Line 63, Underline is missing from o-benzylbenzoate

Col 7, Line 66, Underline is missing from o-benzoyl and m-benzyl

Col. 8, Line 1, Underline is missing from m-toluyl

UNITED STATES PATENT AND TRADEMARK OFFICE
CERTIFICATE OF CORRECTION

PATENT NO. : 4,080,275

DATED : 3/21/78

INVENTOR(S) : J. M. Photis

It is certified that error appears in the above-identified patent and that said Letters Patent are hereby corrected as shown below:

Col. 8, Line 10, Table , Underline is missing from n-butyl-o-benzoylbenzoate, and n-butyl-m-benzoylbenzoate Col. 8, Line 12, After ACTOMER X· should be X·80

Col. 8, Line 21, Underline is missing from "p"-benzylbenaote

Col. 8, Line 29, Underline is missing from"p"-benzoylbenzoic

Col. 8, Line 41, Underline is missing from "p"benzoyl benzoate

Col. 8, Line 49, "with" should be "which"

Col. 8, Line 54, Underline is missing from "p"-benzoylbenzoate

Col. 8, Line 55, Underline is missing from "p"-benzoyl benzoic

Col. 8, Line 55, para should be underlined

Col. 9, Line 1, Underline is missing from p-benzoylbenzoate

Col. 9, Line 2, Underline is missing from para

Col. 9, Line 14, Underline is missing from "p"-benzoylbenzoate

UNITED STATES PATENT AND TRADEMARK OFFICE
CERTIFICATE OF CORRECTION

PATENT NO. : 4,080,275
DATED : 3/21/78
INVENTOR(S) : J. M. Photis, F. A. Via

It is certified that error appears in the above-identified patent and that said Letters Patent are hereby corrected as shown below:

Col. 9, Line 15, Underline is missing from para-benzoylbenzoic

Col. 9, Line 24, Underline is missing from "p"-benzoylbenzoate

Col. 9, Line 25, Underline is missing from para-benzoylbenzoic

Col. 9, Line 35, Underline is missing from "p"-benzoylbenzoic

Col. 9, Line 43, Underline is missing from "p"-benzoylbenzoate

Col. 9, Line 51, Underline is missing from iso-butyl-"p"-benzoyl benzoate

Col. 9, Line 52, Underline is missing from "p"-benzoylbenzoate trichloride

Col. 9, Line 62, Underline is missing from (4-pentyenyl)-"p"-benzoyl benzoate

Col. 10, Line 3, Underline is missing from N, N-diethyl-"p"-benzoylbenzoic

Col. 10, Line 4, Underline is missing from "p" - benzoylbenzoic

Col. 10, Line 10, Underline is missing from

UNITED STATES PATENT AND TRADEMARK OFFICE
CERTIFICATE OF CORRECTION

PATENT NO. : 4,080,275

DATED : 3/21/78

INVENTOR(S) : J. M. Photis, F. A. Via

It is certified that error appears in the above-identified patent and that said Letters Patent are hereby corrected as shown below:

Col. 10, Line 11, Underline is missing from n-isobutyl-"p"-benzoyl benzamide

Col. 10, Line 17, Underline is missing from N, N-di-n-butyl-"p"-benzoyl benzamide Col. 10, Line 18, Underline is missing from "p"-benzoyl benzoic Col. 10, Line 18, Underline is missing from di-n-butylamine Col. 10, Line 46, Change "oxygen" to "OR"

Col. 11, Line 12, change "nitrogen" to "NHR or NRR"

Signed and Sealed this

Third Day of October 1978

[SEAL]

Attest:

RUTH C. MASON
Attesting Officer

DONALD W. BANNER
Commissioner of Patents and Trademarks